US010179011B2

(12) United States Patent
Garfein et al.

(10) Patent No.: US 10,179,011 B2
(45) Date of Patent: Jan. 15, 2019

(54) STERNAL OSTEOTOMY GUIDE AND STERNAL FIXATION SYSTEM

(71) Applicant: Montefiore Medical Center, Bronx, NY (US)

(72) Inventors: Evan S. Garfein, New York, NY (US); David S. Geller, Katonah, NY (US); Katherine A. Weimer, Evergreen, CO (US)

(73) Assignee: Montefiore Medical Center, Bronx, NY (US)

( * ) Notice: Subject to any disclaimer, the term of this patent is extended or adjusted under 35 U.S.C. 154(b) by 127 days.

(21) Appl. No.: 14/993,156

(22) Filed: Jan. 12, 2016

(65) Prior Publication Data

US 2016/0331388 A1    Nov. 17, 2016

Related U.S. Application Data

(60) Provisional application No. 62/103,257, filed on Jan. 14, 2015.

(51) Int. Cl.
| | | |
|---|---|---|
| *A61B 17/82* | (2006.01) | |
| *A61B 17/68* | (2006.01) | |
| *A61B 17/15* | (2006.01) | |
| *A61B 17/88* | (2006.01) | |
| *A61B 17/17* | (2006.01) | |

(52) U.S. Cl.
CPC ............ *A61B 17/683* (2013.01); *A61B 17/15* (2013.01); *A61B 17/8869* (2013.01); *A61B 17/1789* (2016.11); *A61B 17/823* (2013.01)

(58) Field of Classification Search
CPC ... A61B 17/683; A61B 17/15; A61B 17/8869; A61B 17/1789; A61B 17/823
USPC .................. 606/74–75, 79, 82, 324, 905
See application file for complete search history.

(56) References Cited

U.S. PATENT DOCUMENTS

| 4,279,248 A * | 7/1981 | Gabbay ............... A61B 17/823 24/525 |
|---|---|---|
| 8,668,697 B2 * | 3/2014 | Deslauriers ...... A61B 17/00491 606/282 |
| 2004/0258732 A1 * | 12/2004 | Shikinami ............ A61L 27/446 424/426 |
| 2009/0234357 A1 * | 9/2009 | Morales ............. A61B 17/8076 606/60 |
| 2011/0082459 A1 * | 4/2011 | Aravot ............... A61B 17/1691 606/79 |
| 2011/0295257 A1 * | 12/2011 | McClellan ........... A61B 17/823 606/74 |
| 2012/0323241 A1 * | 12/2012 | McClellan ......... A61B 17/8869 606/74 |
| 2014/0081340 A1 * | 3/2014 | McDaniel ............ A61B 17/844 606/318 |
| 2014/0309699 A1 * | 10/2014 | Houff ................... A61B 17/823 606/281 |
| 2016/0166263 A1 * | 6/2016 | Sauer ................. A61B 17/0206 606/79 |

* cited by examiner

*Primary Examiner* — Zade Coley
*Assistant Examiner* — Jessica Weiss
(74) *Attorney, Agent, or Firm* — Amster, Rothstein & Ebenstein LLP

(57) ABSTRACT

Systems and methods are described for a sternal osteotomy guide and sternal fixation system.

18 Claims, 16 Drawing Sheets

STERNAL OSTEOTOMY GUIDE AND STERNAL FIXATION SYSTEM

CROSS-REFERENCE TO RELATED APPLICATION

This application claims the benefit of U.S. Provisional Patent Application No. 62/103,257, filed on Jan. 14, 2015, the content of which is herein incorporated by reference into the subject application.

BACKGROUND OF THE INVENTION

Throughout this application various publications are referred to in superscripts. Full citations for these references may be found at the end of the specification before the claims. The disclosures of these publications are hereby incorporated by reference in their entireties into the subject application to more fully describe the art to which the subject application pertains.

Midline axial sternotomy, first described by Milton in 1887 and reintroduced by Julian and Associates in 1957,[1] is the most frequently performed osteotomy worldwide[2], and is the preferred technique for exposure of the heart and great vessels. Despite its advantages, sternal wound complications may occur. Sternal dehiscence can occur in 0.2% to 5% of patients due to poor wound healing and surgery related factors.[3-5]

Sternal dehiscence and deep sternal wound infection (DSWI) are post-sternotomy wound complications that result in significant morbidity and mortality as well as prolonged hospital stay and increased cost to patients who undergo cardiac surgery. The reported prevalence of this complication ranges from 1-5% with reported associated mortality of up to 25%.[6,7] While relatively rare, when they do occur these complications can be severe and costly.

Numerous preoperative and operative risk factors have been identified as predictors of DSWI following cardiac surgery. These include obesity, diabetes mellitus, chronic obstructive pulmonary disease, smoking, steroid use, New York Heart Association functional class IV, osteoporosis, immunosuppression, and previous sternotomy. Operative risk factors include bilateral internal mammary artery harvest, prolonged cardiopulmonary bypass time, and transverse sternal fractures.[8] Additionally, patients with multiple known risk factors or off midline sternotomy have been identified as high risk for sternal dehiscence.[9,10]

Primary reinforcement, an alternative technique to traditional closure by wire cerclage, has been advocated for high-risk patients. Primary sternal plating, stainless steel coils, cables, or recently, a sternal synthesis device are cited as increasing sternal stability and thereby potentially reducing wound infection rates.[9,10] The decision to employ alternative techniques and materials depends on the surgeon's ability to identify high risk patients who would benefit from such primary reinforcement. However, alternative techniques to prevent faulty sternotomy have not been thoroughly addressed in the literature. There are no identified patents that address the issue of asymmetric osteotomy of the sternum with a cutting guide. The present invention addresses the need for improved treatment procedures and apparatus.

SUMMARY OF THE INVENTION

Systems and methods are described for a sternal osteotomy guide and sternal fixation system. Preferably, a sternal fixation system includes one or more non-bioresorbable intra-sternal shims (1), one or more tie members (2), one or more pairs of brackets (3), and, optionally, a ratchet gun (11). Preferably, the shim (1) is configured to be placed between sternal halves and to provide anteroposterior stability once the sternal halves have been pulled together. Preferably, the shim (1) has a relatively thicker or wider center portion than its lateral sides. Preferably, an elongated tie member (2) is attached to or passes through the shim (1). Preferably, the tie (2) has a first end portion that includes a first gear rack (4) on a surface thereof, and a second end portion that includes a second gear rack (5) on a surface thereof. Preferably, teeth forming the first (4) and second (5) gear racks slope in opposing directions. Preferably, the pair of brackets (3) are configured to distribute pressure at a cortical interface thereof and each pair includes a central ratcheting mechanism operable to interface with the first or second tie gear racks (4,5). Preferably, the ratchet gun (11) provides uniform tightening of the pair of brackets (3).

Preferably, the sternal cutting guide (6) comprises a cutting slot (7) adjustable in the cranio-caudal direction of the sternum, wherein the cutting slot (7) allows passage of a sternal saw; hooks (10) for fixing the cutting guide (6) to a patient; and optionally, drilling eyelets (8) for drilling at multiple positions on both sides of the sternum.

The devices described herein can be used in methods of fixating the sternum of a patient following sternal osteotomy where the methods include creating a midline sternal osteotomy; drilling holes in the anterior sternal cortex for passage of shim ties (2); placing one or more non-bioresorbable intra-sternal shims (1) between halves of the cut sternum; passing needles attached to the shim ties (2) from intramedullary to extracortical portions of the sternum; removing the needles from the shim ties (2) leaving a portion of the shim tie (2) protruding from the sternum; positioning on each side of the sternum one of a pair of brackets (3) on the ties (2) for each shim (1); and tightening each pair of brackets (3) using the ratchet gun (11), thereby fixating the sternum of the patient following sternal osteotomy.

DETAILED DESCRIPTION OF THE INVENTION

Figure 1:
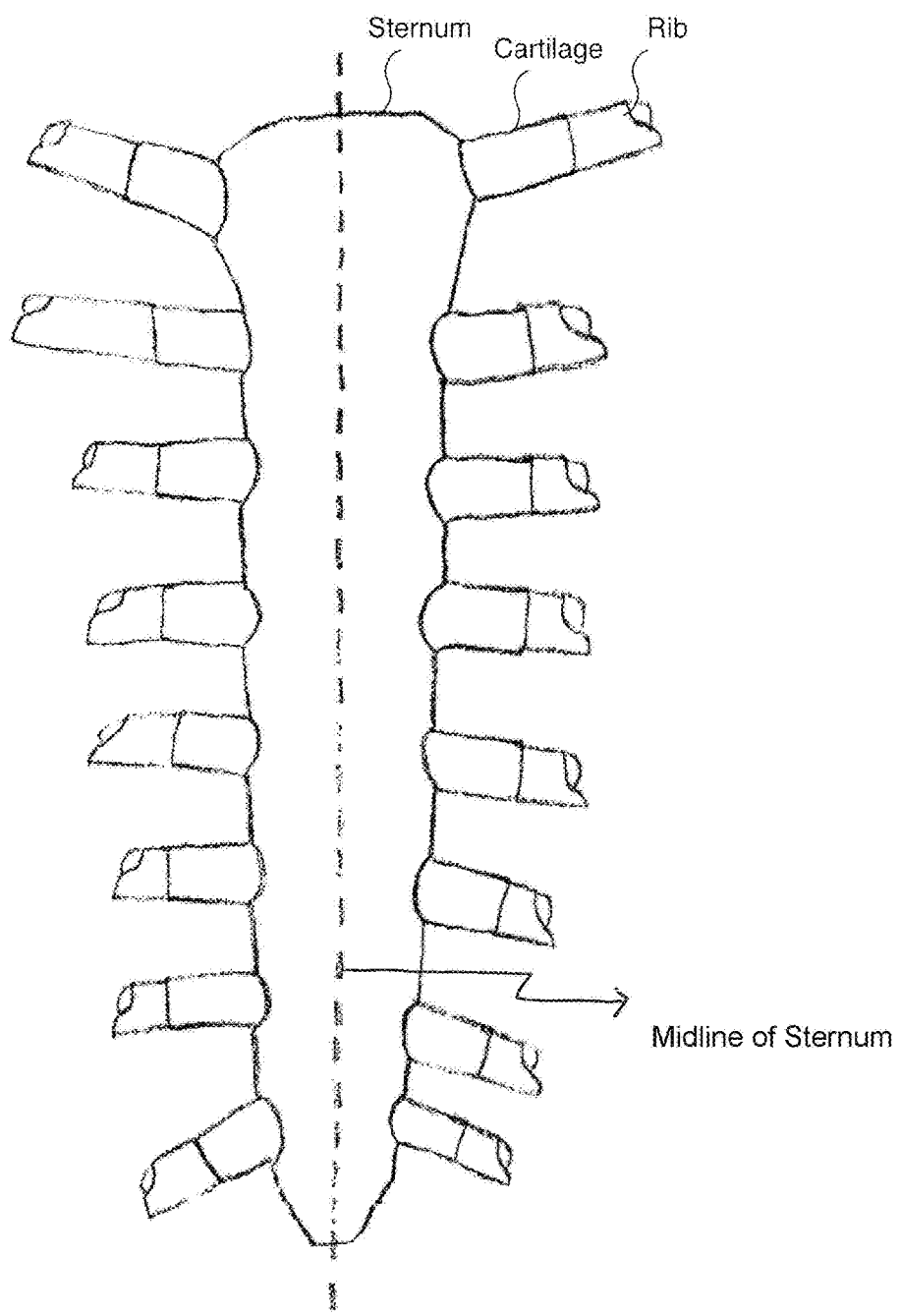
FIG. 1. Illustration of a front view of a sternum, with the rib attachments. The sternum osteotomy guide can be positioned on the sternum to osteotomize at the midline (along the dotted line).
Figure 2:
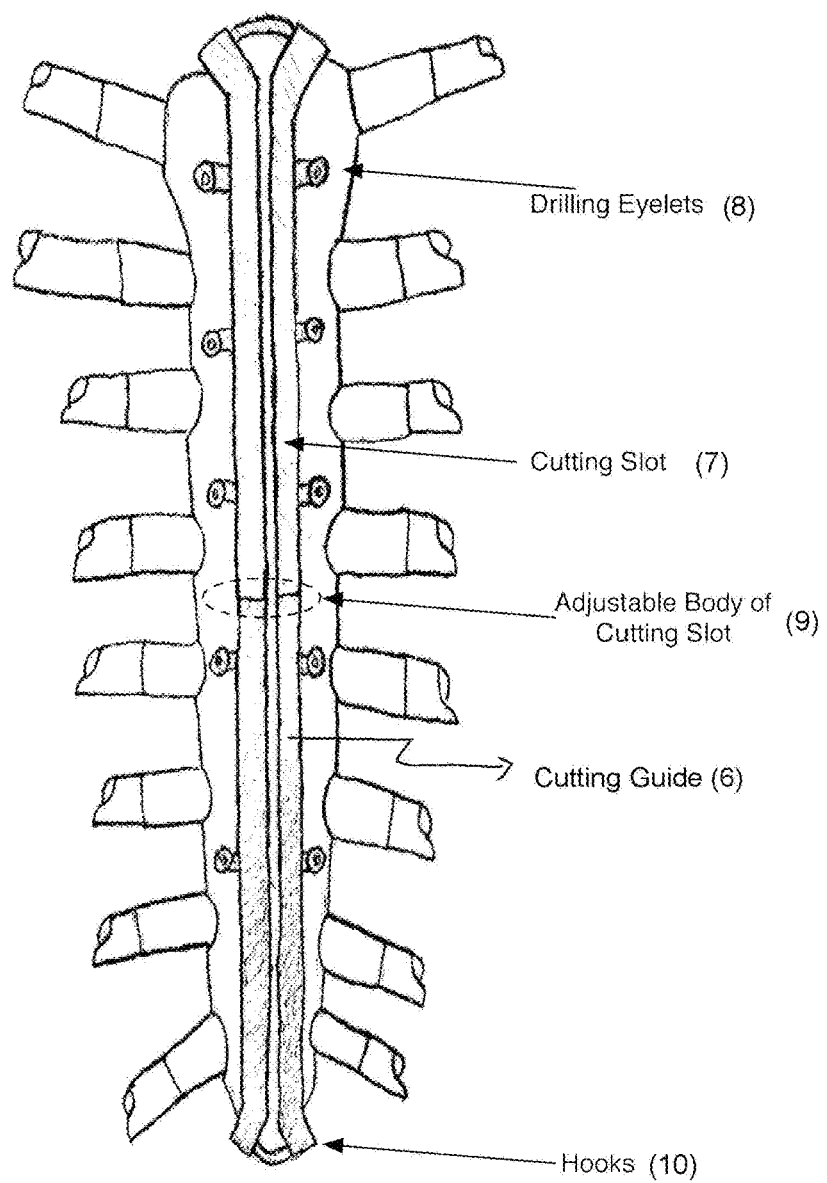
FIG. 2. Illustration of an example of a sternal osteotomy cutting guide (6) placed on the sternum to facilitate osteotomization of the sternum at the midline and eyelets (8) for drilling holes to accommodate the ties (2) used to reapproximate the sternal halves. Cutting slot (7), adjustable body of cutting slot (9) and hooks (10) are illustrated.
Figure 3:
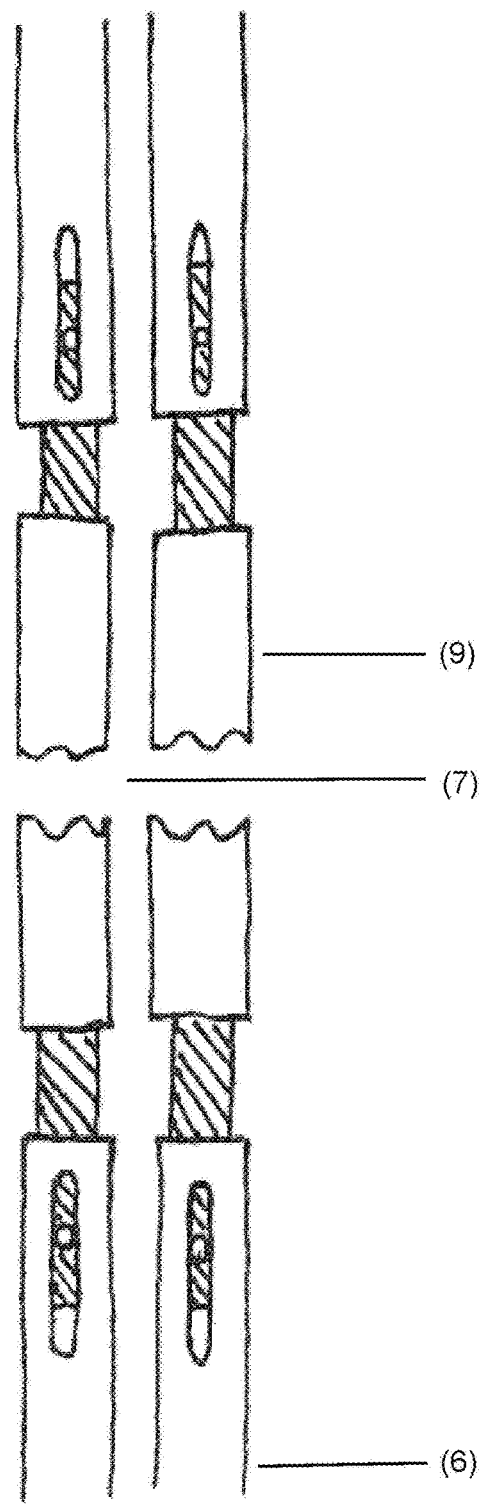
FIG. 3. Illustration of an example of a top view of an adjustable body (9) of a cutting slot (7) of a sternal osteotomy cutting guide (6), which is needed to accommodate sternums of different lengths.
Figure 4:
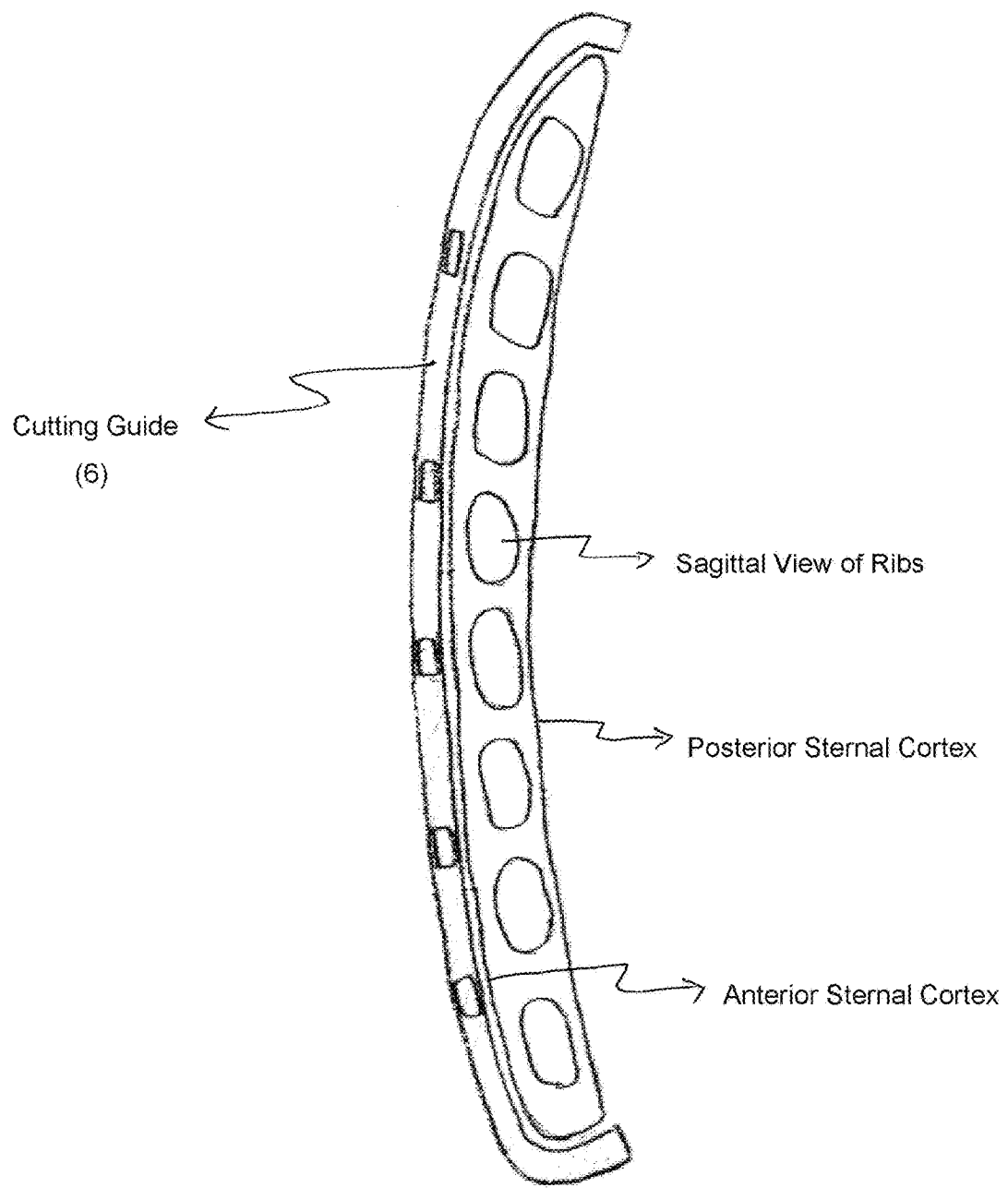
FIG. 4. Illustration of an example of a side view of a sternum osteotomy cutting guide (6) positioned on a sternum.
Figure 5:
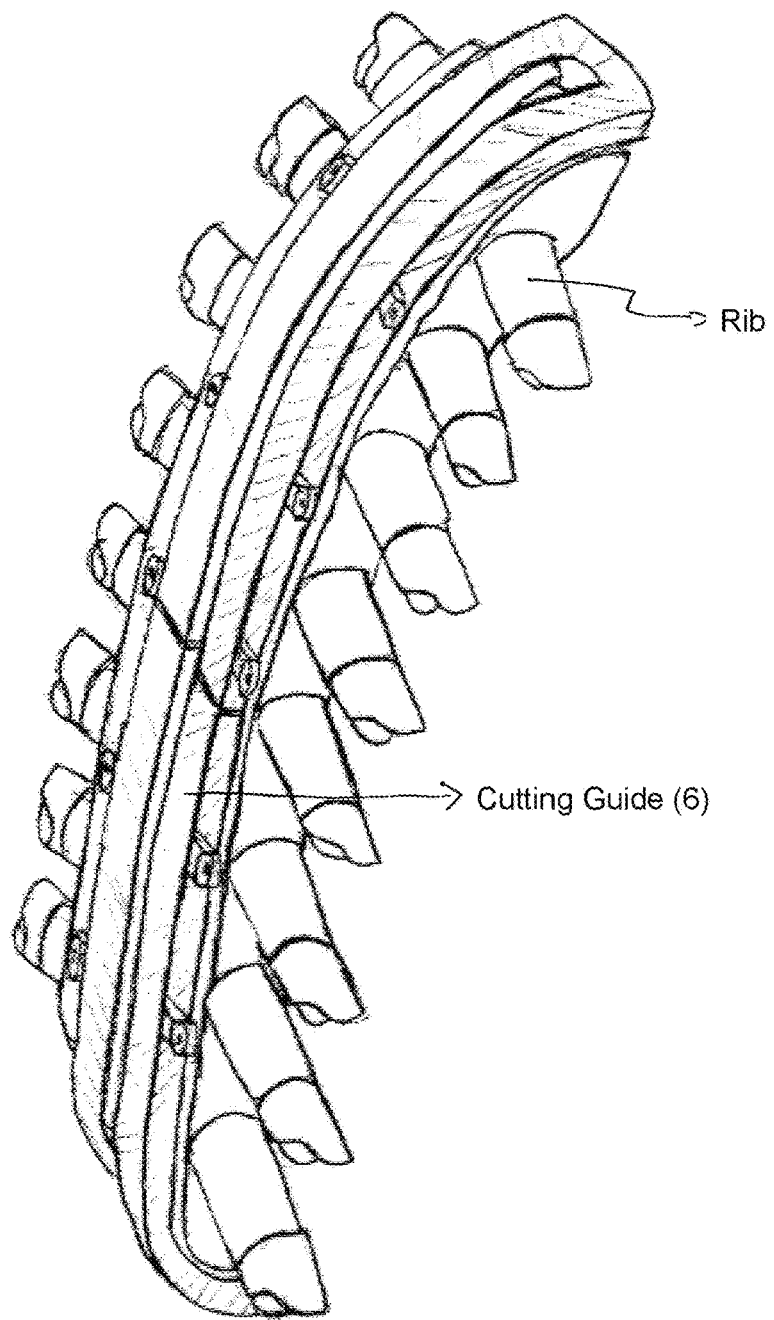
FIG. 5. Illustration of an example of an isometric view of a sternum osteotomy cutting guide (6) positioned on a sternum.
Figure 6:
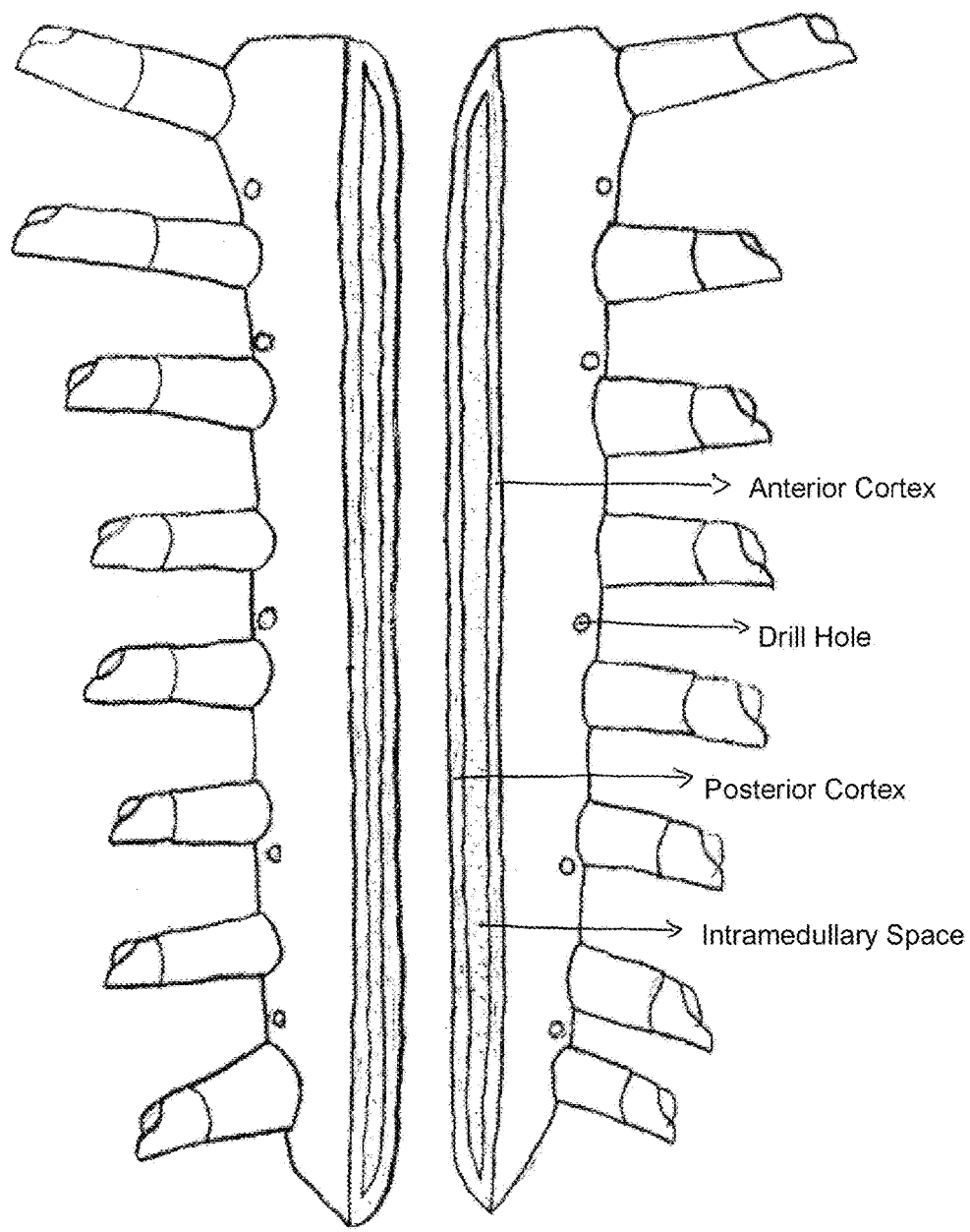
FIG. 6. Illustration of an example of a front view of a completed sternal osteotomy with the sternal osteotomy guide removed. The anterior and posterior cortices of the sternum are illustrated as is the intramedullary space where the shims (1) will be located.
Figure 7:
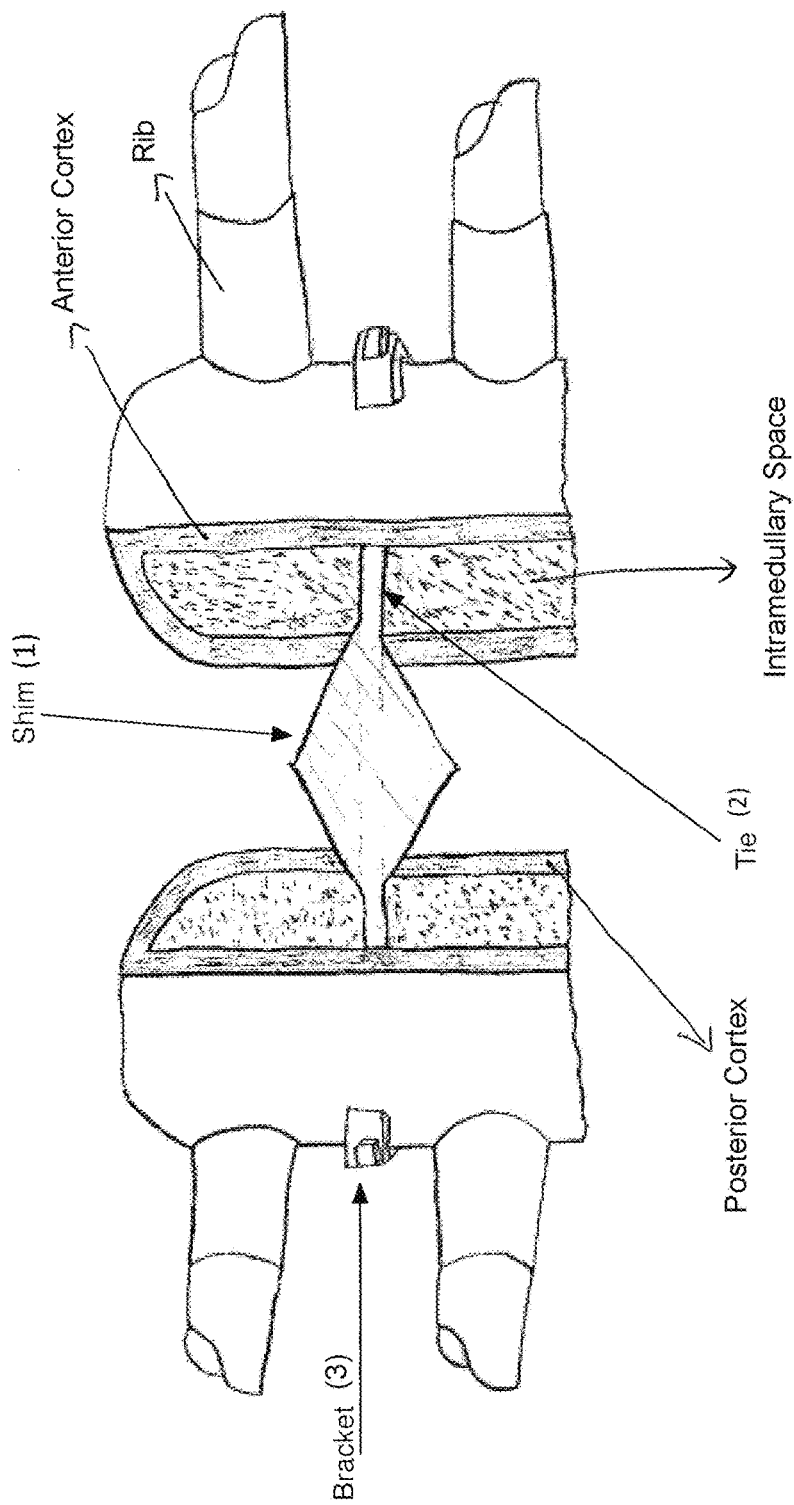
FIG. 7. Illustration of an example of a front view of a sternal fixation system showing shims (1), ties (2) and brackets (3) applied. The shims and the majority of the ties are completely intramedullary, reducing the amount of hardware external to the sternum.
Figure 8:
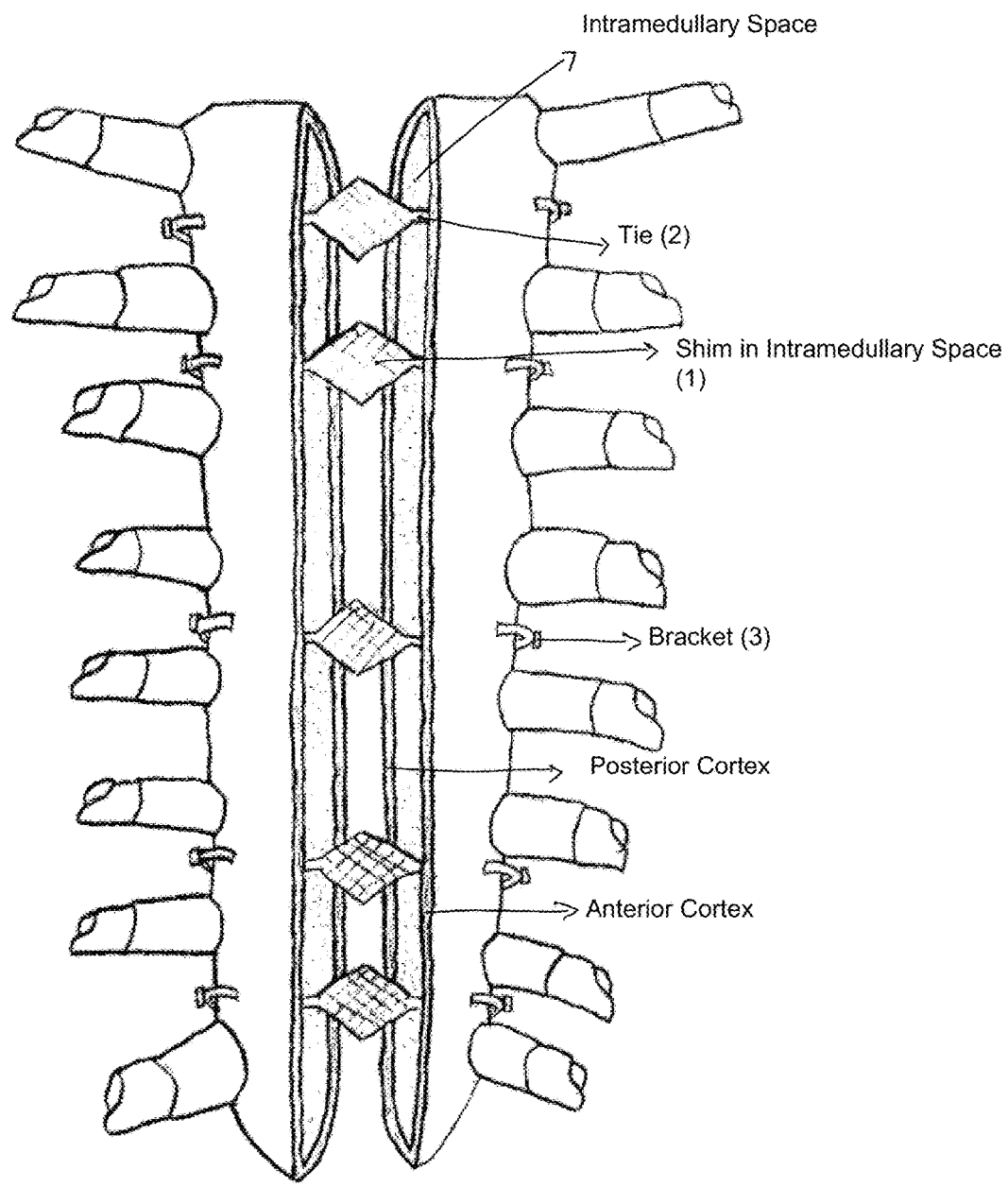
FIG. 8. Illustration of an example of a front view of a sternal fixation system showing shims (1), ties (2) and brackets (3) placed in multiple locations on the sternum.
Figure 9:
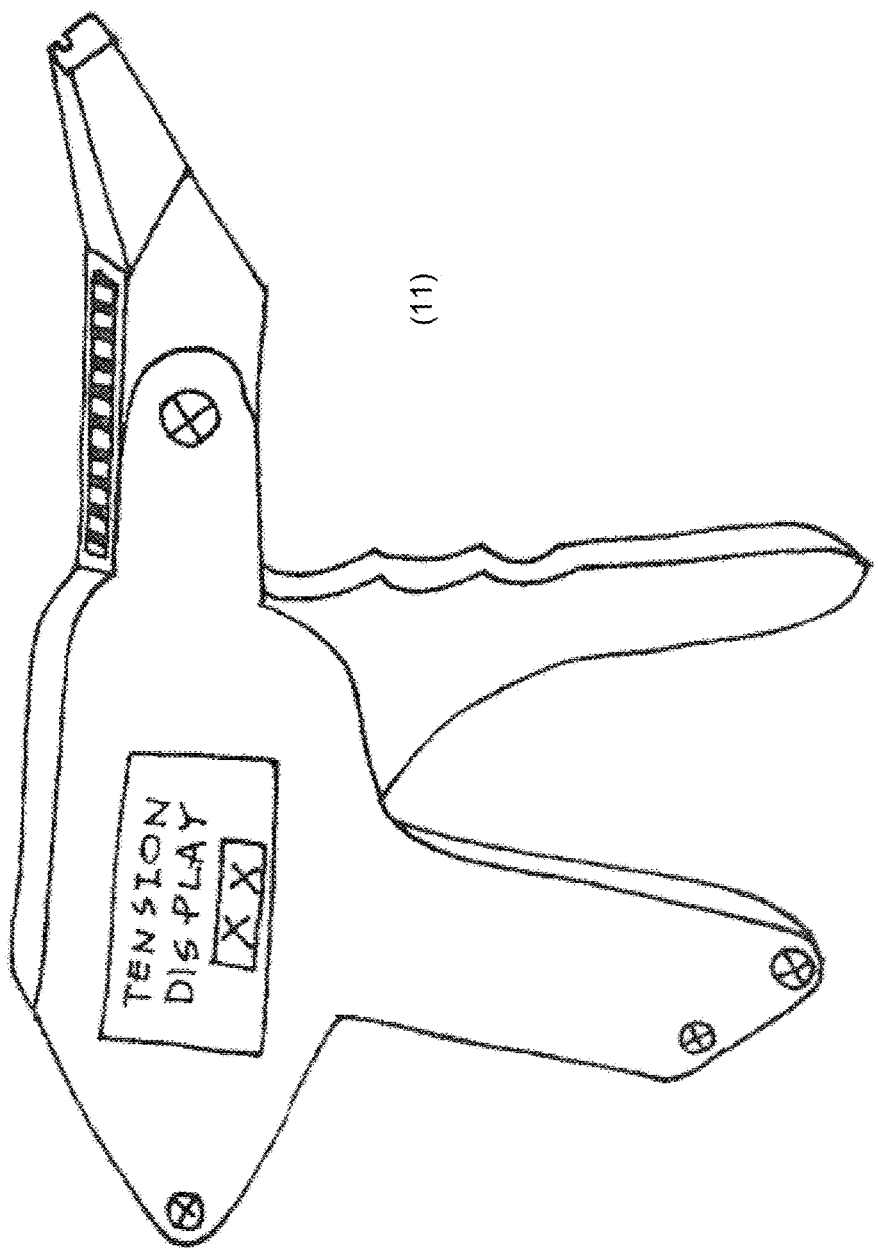
FIG. 9. Illustration of an example of a side view of a ratchet gun (11) that can be used to attach brackets (3) to ties (2) at a uniform tension.
Figure 10:
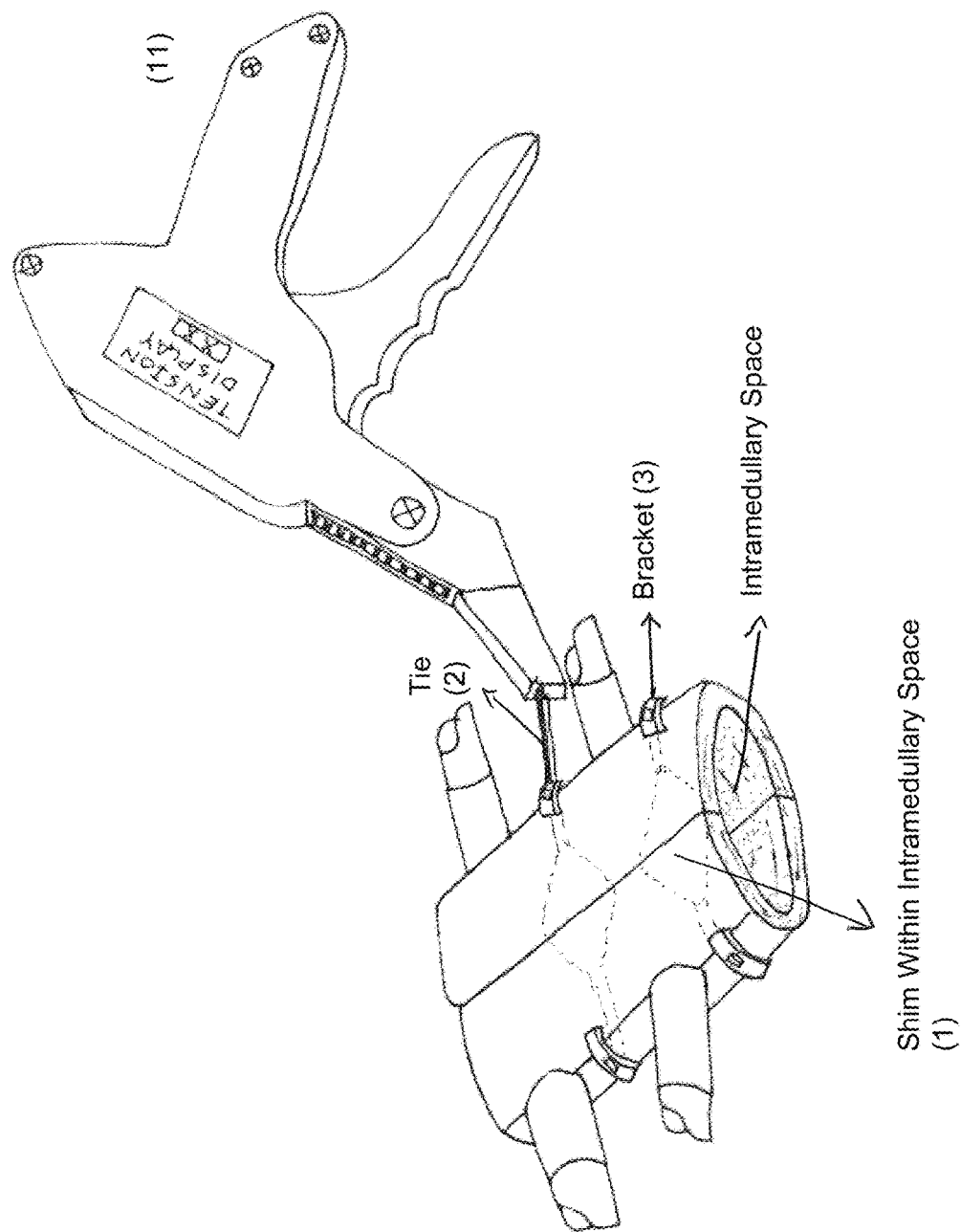
FIG. 10. Illustration of an example of an isometric view of a sternum closed with a shim (1) placed inside the sternum, brackets (3) on lateral sides of the sternum and ties (2) tightened. Ratchet gun (11).
Figure 11:
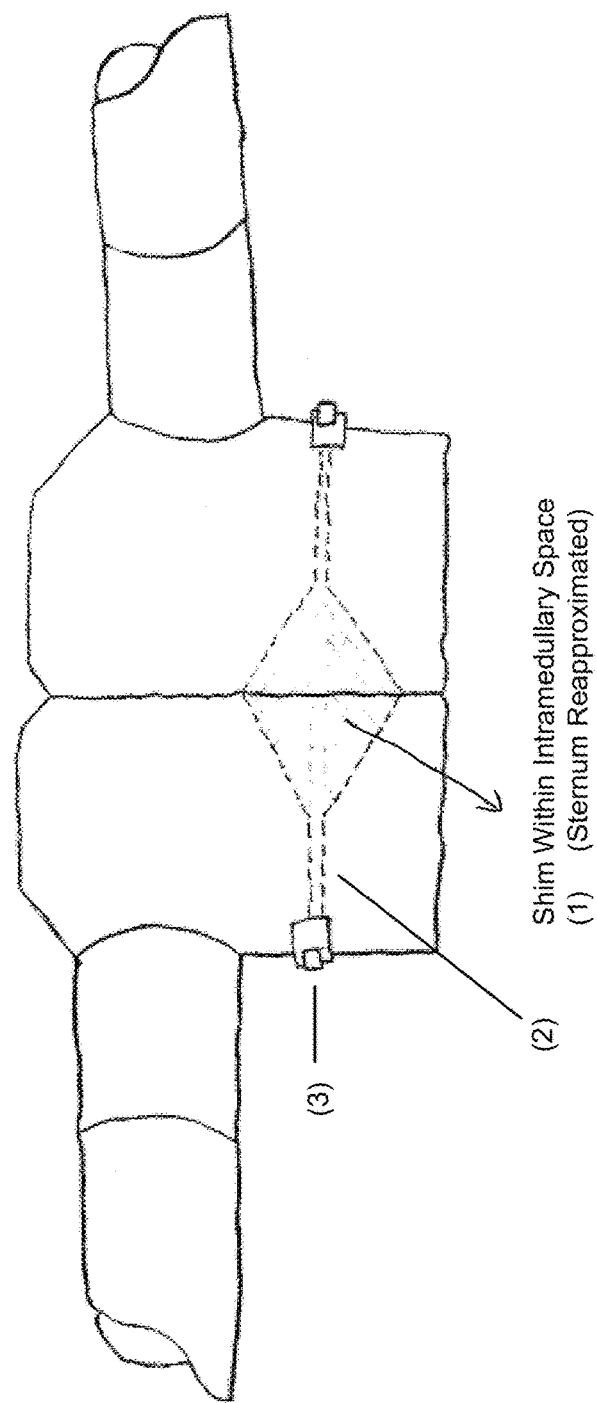
FIG. 11. Illustration of an example of a shim (1) centered in the intramedullary canal of a sternum. Tie (2); bracket (3).
Figure 12:
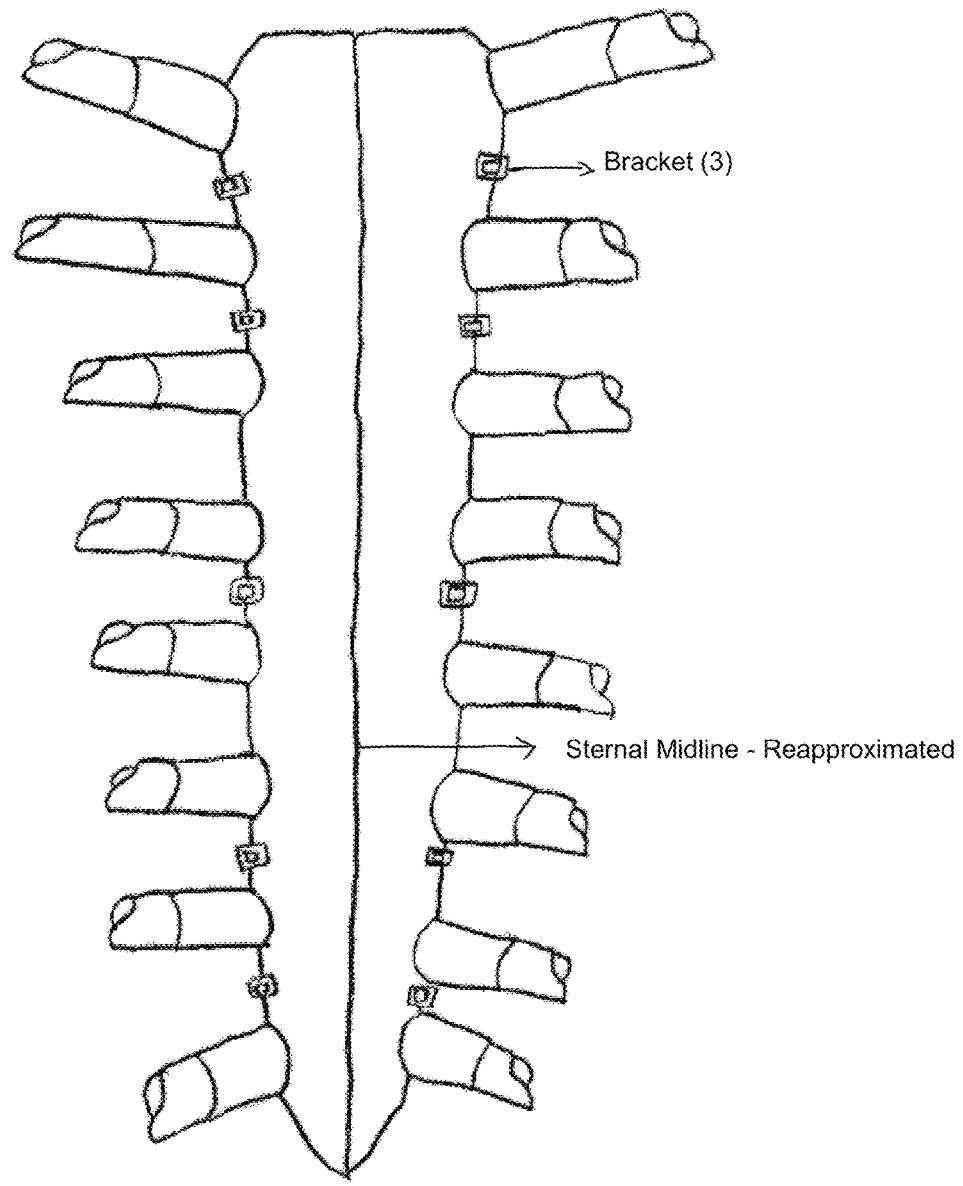
FIG. 12. Illustration of an example of a front view of a sternum closed with 5 shims (1) placed on the inside of the sternum (shims hidden from view by the anterior sternal cortex), brackets (3) on lateral sides of the sternum and ties (2) tightened.
Figure 13:
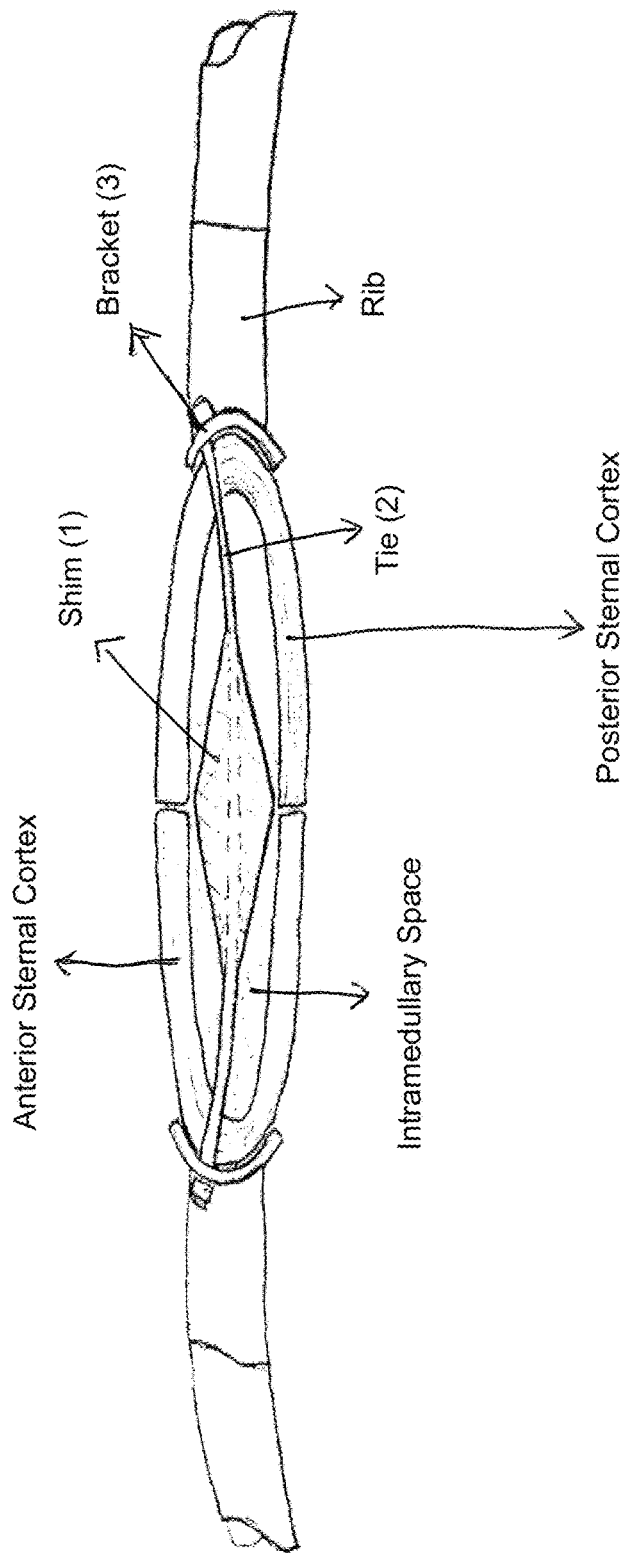
FIG. 13. Illustration of an example of a cross-sectional view of a sternum closed with a shim (1) placed inside the sternum, brackets (3) on lateral sides of the sternum and ties (2) tightened.
Figure 14:
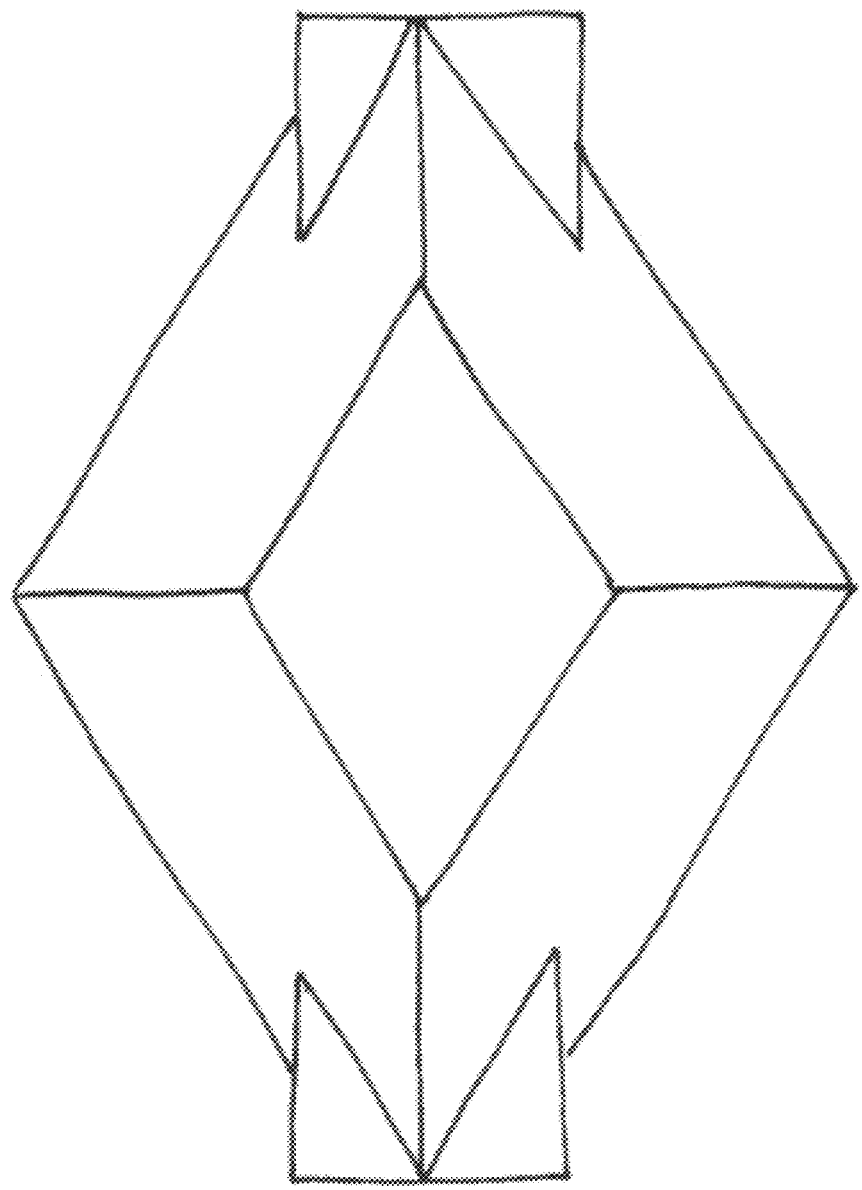
FIG. 14. Illustration of an example of a top view of a shim (1) having a three dimensional shape that is thicker in its middle than edges and having attachment sites for ties (2).
Figure 15:
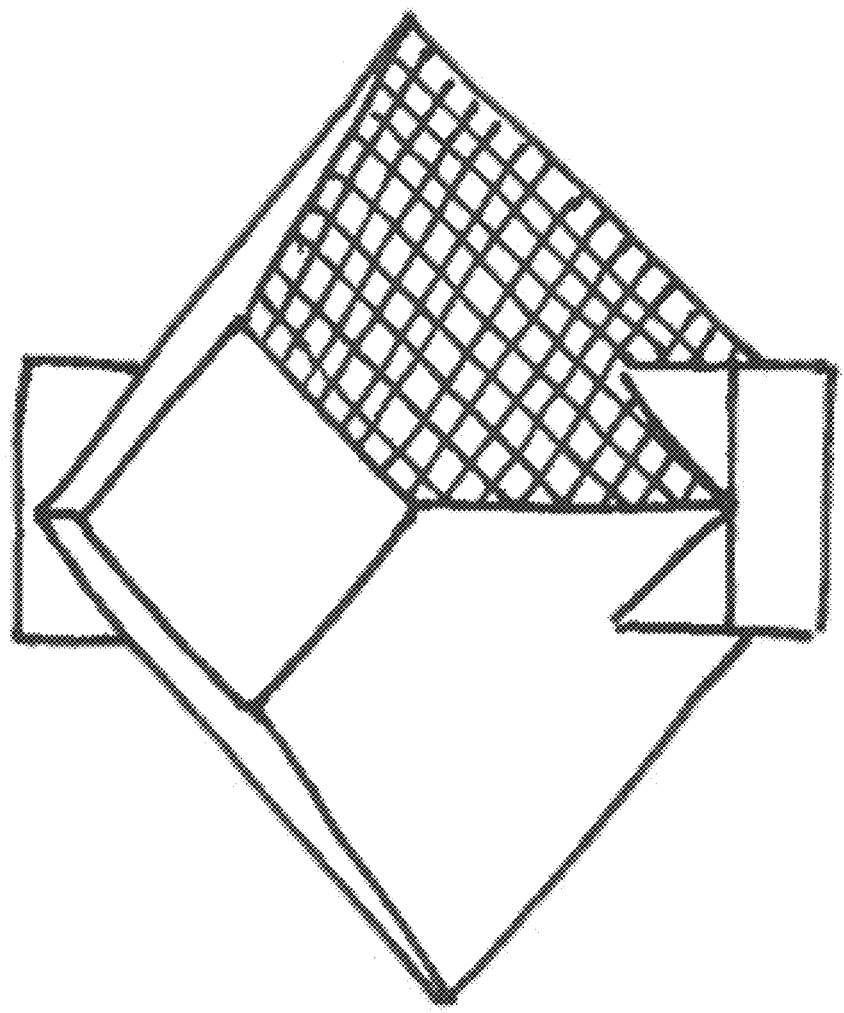
FIG. 15. Illustration of an example of an isometric view of a shim (1) that may be solid, porous or meshed.
Figure 16:
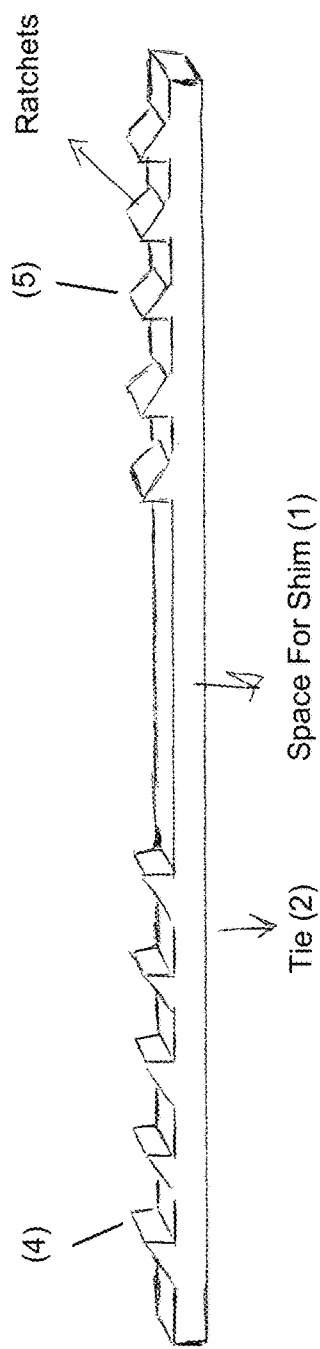
FIG. 16. Illustration of a ratcheted tie (2) with a space for (1) shim. A first integrated gear rack is formed by a first plurality of teeth that slope in a first direction (4) and a second integrated gear rack is formed by a second plurality of teeth that slope in a second direction (5) opposing the first direction.

Systems and methods are described for a sternal osteotomy guide and sternal fixation system. The purpose of the sternal osteotomy guide and sternal fixation system is to rigidly fix the hemi-sternal bones, providing both transverse compression and anteroposterior stability. The fixation method must allow rapid re-entry into the chest in the event of a post-operative, intra-thoracic catastrophe. Total time for creation of the midline sternotomy and closure using the most commonly employed current methods is approximately 10-15 minutes. Any technique that replaces these methods must be as fast or faster, relatively inexpensive, and provide fixation at least as efficiently. An ideal solution would not require the use of devices or techniques overtly foreign to the cardiac surgeon. An ideal method would provide the surgeon with uniformity of compression and minimal foreign material, case-to-case.

The sternal fixation system described in this application addresses major points of weakness in the current methods. First, a reusable, adjustable cutting guide (6) is used to create a midline osteotomy, thereby reducing the risk of DSWI due to asymmetric osteotomy. This same cutting guide (6) is used to pre-drill the holes in the anterior sternal cortex for passage of the shim ties (2) at the completion of the procedure. Once the procedure is complete, needles attached to the shim ties (2) are passed from intramedullary to extracortical and then cut off, leaving only the zip-tie portion of the shim tie (2) sticking out of the antero-lateral cortex of the sternum. A sternal bracket (3) is then slid down, flush to the sternum on the non-surgeon side of the table. The surgeon then uses a calibrated gun (11) to fix a second bracket (3) also flush to the sternum on his or her side of the table. The shims (1) through which the ties (2) pass are intra-sternal.

Preferably, the sternal fixation system includes a non-bioresorbable intra-sternal shim (1), a tie member (2), a pair of brackets (3) and, optionally, a ratchet gun (11). The shim (1) can be configured to be placed between sternal halves and to provide anteroposterior stability once the sternal halves have been pulled together. The shim (1) can have a relatively thicker center portion than its lateral sides. The tie member (2) can be attached to or passed through the shim (1). A first end portion of the tie member (2) can include a first integrated gear rack (4) on a surface thereof. A second end portion of the tie member (2) can include a second integrated gear rack (5) on a surface thereof. Preferably, the teeth forming the first (4) and second (5) integrated gear racks slope in opposing directions. Preferably, brackets (3) are configured in pairs to distribute pressure at a cortical sternal interface thereof, and each pair includes a central ratcheting mechanism operable to interface with the first integrated gear rack (4) or the second integrated gear rack (5). Preferably, the ratchet gun (11) provides uniform tightening of the pair of brackets (3).

Preferred, non-limiting features of the preferred sternal cutting guide (6) and sternal fixation system are described in the following.

Sternal Cutting Guide (6)
Made of stainless steel or titanium material
Reusable
Typical use for adults (16+)
Also available in pediatric sizes
Comes in small, medium and large sizes (optional)
Made up of the following components:
    1. Cutting Slot (7)
        a. Allows passage of sternal saw-adjustable kerfs
        b. Adjustable (9) in the cranio-caudal direction
        c. Flat or slightly curved in the cranio-caudal direction
        d. Has tension in adjustable slot (9)
        e. Release mechanism for tension
        f. Mechanism for determining midline position relative to sternum
        g. Parallel membranes at standard or variable width to form cutting slot (7)
    2. Hooks (10)
        a. Fix beneath sternal notch and at xiphoid.
        b. Shaped in "Y" pattern to allow for insertion/exiting of traditional sternal saw
    3. Drilling Eyelets (8) (optional)
        a. Bilateral
        b. 4-8 pairs of evenly spaced eyelets (8) at same level on either side of sternum
        c. Angled to drill through single cortex of sternum (allow unicortical penetration)
        d. Come out from side of cutting slot (7)
        e. Designed to place hole at multiple distances lateral from osteotomy site (e.g., 1, 1.5, 2 cm, etc.)
        f. Left and Right eyelets (8) are parallel
        g. Provides drill stop to disallow bicortical penetration
        h. Some holes positioned on top slider and some on bottom slider (e.g., 4 on top, 4 on bottom)
        i. Guide position, angulation and depth of hole.

Sternal Fixation System
Made of multiple materials
Not reusable
Typical use for adults (16+)
Available for pediatric patients
Comes in small, medium and large sizes (optional)
Made up of the following components:
    1. Ties (2)
        a. Made of plastic (e.g., polyether ether ketone (PEEK)) or stainless steel
        b. Have zip tie-like ratcheting system c. Zip ties are in opposing direction on opposite sides of shim (1)
d. Attached to cutting needle on both ends
e. Length approximately 20-45 cm
f. Attach to or pass through shim (1)
2. Shims (1)
   a. Non bioresorbable
   b. Titanium impregnated (with biological/bioactive substance), Titan Mesh or non-impregnated porous polyethylene (MEDPOR®)-like material
   c. Shim (1) allowed to slide along or fixed to tie (2)
   d. Shim (1) is three-dimensionally thinner on lateral sides, thicker in center
   e. Come in small, medium and large sizes
   f. If tie (2) is passing through shim (1), then shim (1) will have central slot or tunnel
   g. Microbarbs in opposing directions to encourage better fixation inside sternal medullary canal (optional)
3. Brackets (3):
   a. Central ratcheting mechanism (CRM) Tightened via rachet gun (11) or by hand
   b. Buttons with mechanism to attach to zip ties
   c. 2 deformable metal tabs (alternate to option b)
      i. Low profile
      ii. Malleable to make them flush with sternal border—whether it is on the lateral or anterior surface of the sternum
4. Ratchet Gun (11) (optional)
   a. Load variable
   b. Similar to zip tie gun
   c. Reusable or non reusable
   d. Used to tighten brackets (3) on tie (2) to sternum
   e. Provides standard tightening every time
   f. Stores and loads brackets (3) (optional)
   g. Angled and narrowed snout (optional)
   h. Real time tension display
5. Disassembling Tool (optional)
   a. Cutting mechanism to unfasten brackets (3) from ties (2)
   b. Rongeur-like cutting tool to capture unfastened brackets (3).

Asymmetric osteotomy of the sternum is a major cause of DSWI (deep sternal wound infection) which, in turn, is a major cause of post-cardiac surgery morbidity and mortality as well as cost to the health care system. Using the sternal osteotomy guide to guide a midline osteotomy, the complications from DSWI should decrease. The present systems and methods include the following advantages:

Monocortical drill holes provide access for placement of a fast, simple, transversely oriented fixation system
Fast, cheap, non-bioreactive, allows for rapid re-entry into chest, uniform closure pressure, A-P (anteroposterior) as well as transverse compression
Ties (2)—Fast, cheap, non-reactive
Shims (1)—Provide A-P stability of sternum
Brackets (3)—Distribute pressure at cortical interface; decrease likelihood of cut-through
Ratchet Gun (11)—Provides uniform tightening.

REFERENCES

1. Dalton M L, Connally S R, Sealy W C. Julian's reintroduction of Milton's operation. Ann Thorac Surg 1992; 53:532-533.
2. Raman J, Song D H. Bolotin G, Jeevanandam V. Sternal closure with titanium plate fixation—a paradigm shift in preventing mediastinitis. Interact Cardiovasc Thorac Surg, 2006; 5:336-339.
3. Casha A R, Yang L, Kay P H, Saleh M, Cooper G J. A biomechanical study of median sternotomy closure technique. Eur J Cardiothorac Surg 1999: 15:365-9.
4. Olbrecht V A, Barreiro C J, Bonde P N, Williams J A, Baumgartner W A, Gott V L, Conte J V. Clinical outcomes of noninfectious sternal dehiscence after median sternotomy. Ann Thorac Surg. 2006: 82:902-907.
5. Robicsek F, Fokin A, Cook J, Bhatia D. Sternal instability after midline sternotomy. Thorac Cardiovasc Surg 2000; 48:1-8.
6. Gummert J F, Barten M J, Hans C, Kluge M, Doll N, Walther T, Hentschel B, Schmitt D V, Mohr F W, Diegeler A. Mediastinitis and cardiac surgery—an updated risk factor analysis in 10,373 consecutive adult patients. Thorac Cardiovasc Surg 2002; 50:87-91.
7. Sachithanandan A, Nanjaiah P, Nightingale P, Wilson I, Graham T, Rooney S, Keogh B, Pagano D. Deep sternal wound infection requiring revision surgery: impact on mid-term survival following cardiac surgery. Eur J Cardiothorac Surg 2008; 33:673-678.
8. Snyder C W, Graham L A, Byers R E, Holman W L. Primary sternal plating to prevent sternal wound complications after cardiac surgery: early experience and patterns of failure. Interact Cardiovasc Thorac Surg. 2009; 5:763-6.
9. Zeitani J, Penta de Peppo A, Moscarelli M, Guerrieri Wolf L, Scafuri A, Nardi P, Nanni F, Di Marzio E, De Vico P, Chiariello L. Influence of sternal size and inadvertent paramedian sternotomy on stability of the closure site: a clinical and mechanical study. J Thorac Cardiovasc Surg. 2006; 132:38-42.
10. Zeitani J, Penta de Peppo A, Bianco A, Nanni F, Scafuri A, Bertoldo F, Salvati A, Nardella S, Chiariello L. Performance of a novel sternal synthesis device after median and faulty sternotomy: mechanical test and early clinical experience. Ann Thorac Surg. 2008; 85(1):287-93.

What is claimed is:
1. A sternal fixation system comprising:
one or more non-bioresorbable intra-sternal shims (1) dimensioned and configured to fit completely within the intramedullary space between cut portions of the sternum so that the one or more shims are fully embedded within the intramedullary space once the sternal portions are pulled together, each shim (1) having a central portion and lateral sides, the central portion having a first thickness and the lateral sides having a second thickness, wherein the first thickness is greater than the second thickness;
one or more tie members (2) attached to or passing through each shim (1), each tie member (2) having a first end portion and a second end portion and including a first integrated gear rack on a surface of the first end portion and a second integrated gear rack on a surface of the second end portion, wherein the first integrated gear rack is formed by a first plurality of teeth that slope in a first direction (4) and the second integrated gear rack is formed by a second plurality of teeth that slope in a second direction (5) opposing the first direction; and
one or more pairs of brackets (3) configured to distribute pressure at a cortical interface thereof and each pair having a central ratcheting mechanism operable to interface with the first integrated gear rack or the second integrated gear rack.

2. The sternal fixation system of claim 1, wherein the one or more shims (1) are solid, porous or meshed.

3. The sternal fixation system of claim 1, wherein the one or more shims (1) comprise titanium impregnated with a biological or bioactive substance, titanium mesh or non-impregnated porous polyethylene.

4. The sternal fixation system of claim 1, wherein the one or more shims (1) have a triangular shape on one or more sides of the tie member (2).

5. The sternal fixation system of claim 1, wherein the one or more tie members (2) comprise polyether ether ketone or stainless steel.

6. The sternal fixation system of claim 1, further comprising a ratchet gun (11) to provide uniform tightening of the one or more pairs of brackets (3).

7. The sternal fixation system of claim 6, wherein the ratchet gun (11) attaches the one or more pairs of brackets (3) to the one or more tie members (2) at a uniform tension.

8. The sternal fixation system of claim 1, further comprising a sternal cutting guide (6).

9. The sternal fixation system of claim 8, wherein the sternal cutting guide (6) comprises
a cutting slot (7) configured to be adjustable in the cranio-caudal direction of the sternum, wherein the cutting slot (7) is configured to allow passage of a sternal saw; and
hooks (10) configured to fix the sternal cutting guide (6) to a patient.

10. The sternal fixation system of claim 9, wherein the sternal cutting guide (6) comprises stainless steel and/or titanium.

11. The sternal fixation system of claim 9, wherein the cutting slot (7) comprises one or more of:
a flat or slight curvature in the cranio-caudal direction,
a mechanism configured for determining a midline position of the cutting slot (7) relative to the sternum, and
parallel membranes that form the cutting slot (7).

12. The sternal fixation system of claim 9, wherein the hooks (10) are configured to fix beneath the sternal notch and at the xiphoid of a patient, and wherein a pair of the hooks (10) is shaped in a "Y" pattern to allow access of a sternal saw to the cutting slot (7).

13. The sternal fixation system of claim 9, wherein the sternal cutting guide (6) further comprises drilling eyelets (8) configured for drilling at multiple positions on both sides of the sternum.

14. The sternal fixation system of claim 1, wherein the one or more shims (1) each have a central slot or tunnel configured to allow one of the one or more tie members (2) to pass through the shim (1).

15. The sternal fixation system of claim 1, wherein the one or more shims (1) have a rhombial shape.

16. The sternal fixation system of claim 1, wherein the one or more shims (1) are configured to provide anteroposterior stability once the sternal portions are pulled together.

17. A method of fixating the sternum of a patient following sternal osteotomy using the sternal fixation system of claim 1, the method comprising:
creating a midline sternal osteotomy;
drilling holes in the anterior sternal cortex for passage of shim ties (2);
placing one or more non-bioresorbable intra-sternal shims (1) between portions of the cut sternum;
passing needles attached to the shim ties (2) from intramedullary to extracortical portions of the sternum;
removing the needles from the shim ties (2) leaving a portion of each shim tie (2) protruding from the sternum;
positioning on each side of the sternum one of a pair of brackets (3) on the shim ties (2) for each shim (1); and
tightening each bracket (3) using a ratchet gun (11),
thereby fully embedding the shims (1) within the intramedullary space and fixating the sternum of the patient following sternal osteotomy.

18. The method of claim 17, wherein an adjustable cutting guide (9) is used to create the midline sternal osteotomy and/or drill holes in the anterior sternal cortex.

* * * * *